(12) United States Patent
Werblin

(10) Patent No.: US 6,413,276 B1
(45) Date of Patent: Jul. 2, 2002

(54) MODIFIED INTRAOCULAR LENS AND METHOD OF CORRECTING OPTICAL ABERRATIONS THEREIN

(75) Inventor: Theodore Werblin, Princeton, WV (US)

(73) Assignee: Emmetropia, Inc., Princeton, WV (US)

( * ) Notice: Subject to any disclaimer, the term of this patent is extended or adjusted under 35 U.S.C. 154(b) by 0 days.

(21) Appl. No.: 09/558,330

(22) Filed: Apr. 26, 2000

(51) Int. Cl.⁷ ................................................. A61F 2/16
(52) U.S. Cl. ...................... 623/6.32; 623/6.11
(58) Field of Search ................. 623/6.11, 6.12, 623/6.24, 6.27, 6.31, 6.32, 6.22; 128/898

(56) References Cited

U.S. PATENT DOCUMENTS

| | | |
|---|---|---|
| 4,575,373 A | 3/1986 | Johnson |
| 4,787,903 A | 11/1988 | Grendahl |
| 4,838,266 A | 6/1989 | Koziol et al. |
| 5,066,301 A | 11/1991 | Wiley |
| 5,196,027 A | 3/1993 | Thompson et al. |
| 5,222,981 A | 6/1993 | Werblin |
| 5,288,293 A | 2/1994 | O'Donnell, Jr. |
| 5,728,155 A | 3/1998 | Anello et al. |
| 5,777,719 A | 7/1998 | Williams et al. |
| 5,943,117 A | 8/1999 | Van de Velde |
| 5,968,094 A | 10/1999 | Werblin et al. |

OTHER PUBLICATIONS

*Journal of Refractive Surgery*, vol. 15, May/Jun. 1999, Barraquer Lecture 1998, "Why Should Refractive Surgeons Be Looking Beyond the Cornea?" Theodore P. Werblin, MD, PhD.

*Primary Examiner*—Dinh X. Nguyen
(74) *Attorney, Agent, or Firm*—Arent Fox Kintner Plotkin & Kahn, PLLC

(57) ABSTRACT

A method of correcting optical aberrations and abnormalities within the optical system of an eye having an intraocular lens implanted therein. The method includes the step of measuring and determining the extent of the aberrations and abnormalities. Removing at least one removable component of the intraocular lens. Modifying at least one surface of the removable component to eliminate or correct the aberrations and abnormalities. Reinserting the modified removable component within the intraocular lens in the optical system through a same wound formed to originally implant the intraocular lens.

58 Claims, 12 Drawing Sheets

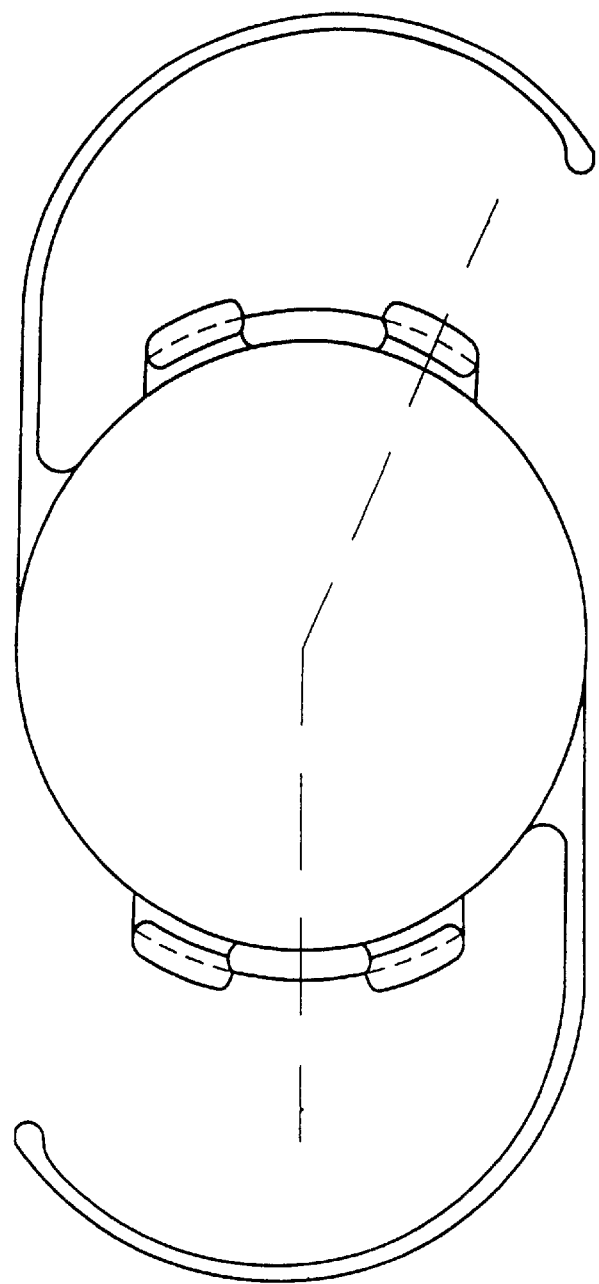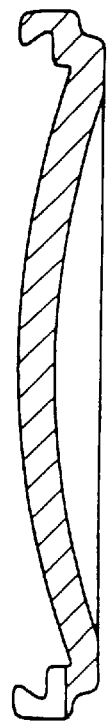
FIG.4A (RELATED ART)
FIG.4B (RELATED ART)

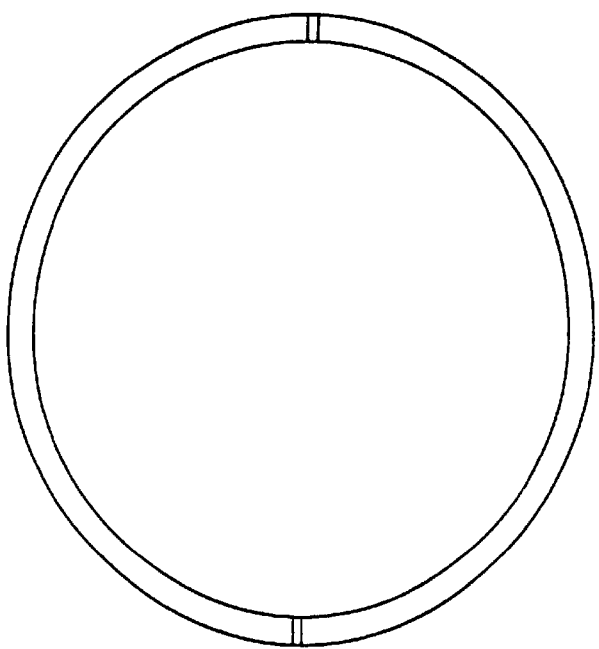
FIG.5A
(RELATED ART)
FIG.5B
(RELATED ART)

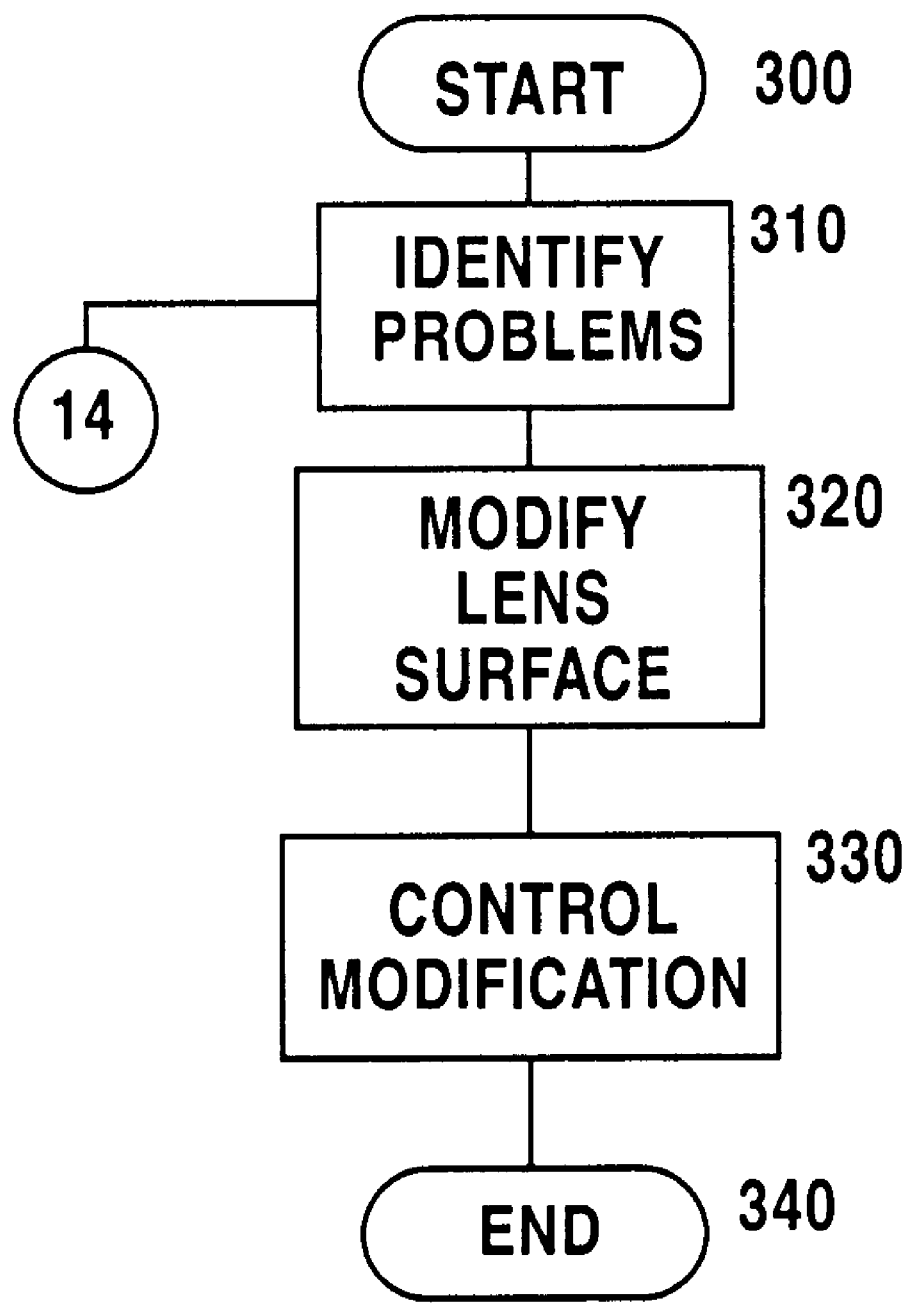

MODIFIED INTRAOCULAR LENS AND METHOD OF CORRECTING OPTICAL ABERRATIONS THEREIN

INCORPORATION BY REFERENCE

The disclosure of U.S. Pat. No. 5,222,981 to Werblin, which issued on Jun. 29, 1993; U.S. Pat. No. 5,968,094 to Werblin et al., which issued on Oct. 19, 1999; and the article entitled Why Should Refractive Surgeons Be Looking Beyond the Cornea?, which was published in the *Journal of Refractive Surgery*, Volume 15, May/June 1999 and authored by the inventor of the instant application are herein incorporated by reference in their entirety.

BACKGROUND OF THE INVENTION

1. Field of Invention

This invention relates to a method for correcting optical aberrations in the optical system of an eye having an intraocular lens. More particularly, this invention relates to a method of correcting optical aberrations and other focusing abnormalities measured by wave front or other such technology to quantify optical aberrations in the optical system of the eye, using a laser, or other apparatus and/or methods of fabricating or modifying a lens, for the optical system of an eye having an intraocular lens.

2. Description of Related Art

The field of refractive surgery has been evolving rapidly during the past few decades. Unfortunately, the current procedures or methods used by most refractive surgeons may not ultimately satisfy the total refractive needs of the patient. Particularly, the most commonly performed refractive surgical procedures, such as, for example, cataract extraction with intraocular lens implantation, in addition to the most recently popularized corneal refractive surgical procedures, such as eximer laser photoblation, have a number of drawbacks and limitations A reason for some of these drawbacks and limitations is the fact that the lack of post-operative refractive accuracy renders these surgical procedures uncompetitive with the already available non-surgical alternatives available to patients, which are commonly known as glasses and contact lenses.

Current refractive cataract surgeons who perform the most common refractive surgical procedure, i.e., routine cataract surgery, demonstrate refractive accuracies in the ±0.75 to ±1.00 diopter (D) range. However, such a refractive accuracy is generally not satisfactory, given an industry established accepted accuracy goal of ±0.25 D. Furthermore, several recent reports analyzing current corneal refractive technologies indicate the presence of a significant amount of preexisting or naturally occurring post-operative, as well as preoperative, image distortion (optical aberration) or degradation, particularly under low light conditions, such as when driving at night.

Because of surgery, as well as the biological and physical behavior of the human eye during and after the various types of intraocular surgery, the predictability at the ±0.25 D level with just a single surgical procedure is virtually impossible 100% of the time. Furthermore, factors like biometry errors, variable wound healing and capsular contraction around the intraocular lenses all contribute to decreasing the ability of the refractive surgeon to be able to achieve the desired refractive accuracy. Accordingly, practitioners in the industry have found that an adjustable intraocular lens (IOL), hereinafter referred to as the MC-IOL (multi-component) or C-IOL (compound), following lens extraction surgery, provides a number of desirable options for the refractive surgeons as well as their patients.

First and foremost, an adjustable IOL allows fine tuning of the initial refractive result by exchange of several optical elements of the lens implant. Accuracies in the ±0.25 D range should be virtually guaranteed for those patients which demand perfect vision. It is very likely IOL technology will continue to evolve in the future. Therefore, it is desirable to provide the patient with the opportunity to undergo an exchange of "old" technology lens components for the new and improved technology. This can only happen if the surgeon has an effective, efficient, and sale method of performing lens element exchanges. Additionally and more importantly, within the months and/or years after any refractive surgical procedure, if the optical properties of the inserted IOL, such as multifocality for example, becomes problematic, the surgeon has the ability to safely exchange the undesirable optical elements of the IOL to reverse or eliminate any optical problems that are not tolerated by the patient.

In 1990, the inventor of this application began to investigate the feasibility of such an adjustable intraocular lens, commonly known as the multi-component intraocular lens, hereinafter referred to as the MC-IOL (FIG. 1), for use following clear lens or refractive cataract surgery, wherein the optical properties of the MC-IOL can be modified at any post-operative time. The base intraocular lens component of the MC-IOL is shown in FIG. 1. The cap (mid) lens attaches to the top of the base lens and holds the third component of the MC-IOL, the sandwich (top) lens, in place as well.

The base intraocular lens 10 and cap 20 each have securing flanges 16, 18 and 20, 24, respectively, extending therefrom. The MC-IOL also comprises at least one sandwich lens 30), as illustrated in FIG. 1. The sandwich lens 30 is positioned on top of the cap 20. See FIGS. 1–2.

The MC-IOL also includes projections 11 and 13 which serve to hold the MC-IOL in place in the human eye, wherein eye tissue (lens capsule) takes hold on the projections. This arrangement permits the base intraocular lens 10 to form a platform upon which the cap 20 can be placed to provide a vehicle to hold the sandwich lens 30. Therefore, during routine cataract surgery, the MC-IOL replaces the crystalline lens of the human eye. Once a patient's eyes have healed after such a surgery, the surgeon can reenter the eye and replace, if necessary, and more than once, the sandwich lens 30 and the cap 20 to modify the optical characteristics until they reach desired levels.

FIGS. 3A–3B illustrate the assembled compound intraocular lens, hereinafter C-IOL, that can be used with a preexisting lens within the human eye. The C-IOL has two components similar to the cap (mid) FIGS. 4A–4B and sandwich (top) FIGS. 5A–5B lens components of the MC-IOL. The preexisting lens can be the crystalline lens of the eye with the C-IOL placed in the sulcus (FIG. 6) or in the anterior chamber angle (FIG. 7). However, the C-IOL can also be used with a conventional IOL and be mounted in the sulcus (FIG. 8), in the anterior chamber angle (FIG. 9), in the anterior chamber with posterior chamber fixation (FIG. 10) or in the anterior chamber with iris fixation (FIG. 11). Thus, a surgeon modifies the optical characteristics of the optical system of the eye by using the cap and sandwich lenses in tandem with the preexisting conventional IOL implant or the crystalline lens of the eye.

A single component, exchangeable (adjustable) anterior chamber lens can be used in combination with a single component posterior chamber lens. (FIG. 12). This enables the adjustment capability for one of the two components and allows more latitude with respect to the space available in the anterior chamber. Both single component conventional nonadjustable anterior chamber and single component conventional nonadjustable posterior chamber refractive intraocular lenses are currently being used with success. In this lens design however, the exchangeable element of the anterior chamber lens component is unique. Finally, the separation of the two lens components might allow an additional refractive capability such as telescopic vision. This might also necessitate the use of either an additional corneal contact lens or spectacle lens or both.

The C-IOL and MC-IOL provide numerous enhanced features. For example, the C-IOL and MC-IOL can each be structured as a monofocal or multifocal optical system, correct astigmatism, as well as comprise ultraviolet light-absorbing, tinted, or other such chemically treated materials.

It should be understood that there are various reasons why an adjustable, MC-IOL or C-IOL is more desirable than a single component implant. In order to achieve all of the permutations and combinations of the astigmatism, multifocality, and spherical correction needed to achieve emmetropia would take an inventory of over ten thousand lenses, whereas with the MC-IOL (multiple components) concept, an inventory of about one hundred components would be necessary. With anterior chamber lenses, progressive encapsulation or engulfment of the lens haptics by uveal tissue in the angle often occurs 1–2 years post-operatively, making removal difficult or impossible. Exchange of iris fixated anterior chamber lenses cannot guarantee precise position or orientation. Posterior chamber lenses similarly cannot be removed because of posterior capsule fibrosis. Easy removal and exchange ability is critical for any customized emmetropic system. Only a specially designed multicomponent lens system allows this.

Therefore, based on the above discussion, a MC-IOL having three elements rather than one permits refractive customization and adjustability for all refractive errors, for all patients, using a minimal number of lens elements or parts and requiring little customization required by the manufacturer. Thus, it has become very important in the refractive surgery art to be able to individualize and/or customize surgery such that the surgeon can easily and safely, as well as accurately, modify the refractive power of an intraocular lens implant.

For an example, U.S. Pat. No. 5,288,293 to O'Donnell, Jr. discloses a method of modifying a single IOL. O'Donnell suggests that the refractive power of a single IOL may be varied before implantation so that the changes can be made in situ by the ophthalmologist after determining the extent of correction required to improve the vision of the patient before the lens is made. However, the surgical implantation procedure itself may create additional optical aberrations which cannot be anticipated preoperatively and thus not accounted for in the primary lens implant.

As such, it may be argued that if a lens can be modified before being implanted, as suggested by O'Donnell, Jr., it should be possible to modify the implanted lens by removing the implanted lens, modifying the lens, and then reimplanting the modified lens into the optical system of the eye. However, although one may theoretically be able to take a lens that is already implanted into the optical system of this eye, remove the implant from the optical system, modify the implanted lens and re-implant the modified lens as suggested by O'Donnell, unfortunately, IOLs are not designed to do this very easily. Furthermore, after a period of time with normal healing, it will become physically dangerous and/or nearly impossible to the patient to accomplish this once the eye tissue takes hold on the capsular fixation holes of the lens. Therefore, such an argument, although theoretically possible, in reality is not practical or safe. A single component intraocular lens, which in general is not designed to be removed and with only two optical surfaces, cannot allow for compensation of sphere, cylinder, cylindrical axis, and all forms of optical aberrations that may be discovered after the initial implantation. Whereas, the multipart IOL will have four removable optical surfaces which could compensate quite adequately for these optical properties.

The inventor of this application invented the previously discussed MC-IOL and C-IOL that are designed specifically to permit the easy exchange of optical elements at a postoperative period without risk to the human eye or the patients beyond that of ordinary intraocular surgery. The easy exchangeability of optical elements is critical because the actual surgery of implanting the lens in the first place, as well as the way the eye might heal after implantation, does create distortion which may not stabilize for several months after the operation. Therefore, the ability to measure and to compensate for that distortion cannot take place until several months after the actual surgery has occurred and could not be predicted prior to the actual surgery occurring. Since the same surgical wound is used for both the primary and secondary operations, additional distortion due to wound healing would not be anticipated as a result of the second operation. Furthermore, the ability to exchange optical elements of a multicomponent or compound intraocular lens can be quite economical compared to removing, modifying, and re-implanting a single component lens, as well as easier to perform.

The MC-IOL has four surfaces available for modification, two piano and two convex. While it is possible to modify any of the four available surfaces, it is preferred that the modification be made only to the piano surfaces. This will avoid interfering with the convex side which may already be used for correction of astigmatism (cylinder) or used as a multifocal lens surface. The same statement applies to the CIOL which has two surfaces available for modification, one of which is piano and the other convex.

SUMMARY OF THE INVENTION

It is an object of this invention to overcome the above-described drawbacks of the related art.

In particular, it is an object of this invention to conduct measurements using existing technology, such as wave front analysis, to determine any residual or new aberrations that are present in an operated eye after the biological healing parameters have stabilized as well as to correct any residual errors in sphere, cylinder or cylindrical axis. Then, the surgeon will be able to go back into the eye through the very opening that was first created to position the implant and modify one, two, or even more existing lens elements within the implanted optical system based on the measurement obtained from the wave front and refractive analysis. Such modifications will preferably be accomplished with a laser, such as an excimer laser or other known or later developed means suitable for creating an optical surface.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein:

FIGS. 4A–4B are top and side views, respectively, of a type of compound intraocular lens-top lens component;

FIGS. 5A–5B are top and side views, respectively, of a type of compound intraocular lens-top lens component;

FIG. 15 is a flow chart illustrating the steps for carrying out the inventive concept of this application according to another embodiment.

DETAILED DESCRIPTION OF PREFERRED EMBODIMENTS

The theory of the use of an adjustable intraocular lens is that once the biology of the intraocular surgery has stabilized, i.e., wound healing, calculation error, and the like, one can adjust or exchange optical elements, both spherical and cylindrical, independent of any additional wound healing or significant calculation error to fine-tune, reverse, or replace any of the original optical features. The exchange of the optical elements is only applicable to multi-component intraocular lenses (MC-IOL) having at least one removable component. A number of known multi-component intraocular lenses exist, such as the lenses illustrated in FIGS. 1–11.

As discussed above, in such a configuration, the posterior lens element of the MC-IOL looks much like a conventional posterior chamber IOL. Several projections are located at the periphery of the optic to hold two anteriorly attached lens elements. This posterior lens element heals into the capsular bag, just like the conventional posterior chamber intraocular lens, and soon becomes a stable, permanent platform for the possible exchange of the two anteriorly attached optical elements during an enhancement operation. The two anterior lens elements have toric, spherical, multi-focal features, and/or spherical aberration corrections.

In the immediate post-operative period, any necessary residual, spherical, or cylindrical corrections can be fine-tuned with an exchange operation using the original surgical wound to re-enter the eye to remove the old, anteriorly attached lens components and to replace them with new optical elements of the appropriate power, style, and orientation. Since the same surgical wound is being used, little or no additional endothelial damage can be expected because that area has already been affected by the primary procedure. That is, the surgeon is not injuring a new area of healthy endothelium. Also, because one is using the same wound, wound healing should not cause any new astigmatic nor any new optical aberrations following the second operation.

Although multiple, intraocular procedures compound the small risk of intraocular surgery, the risk may be justified because at any post-operative time interval, features such as the multi-focal lens design, monovision, quantified residual astigmatism, and optical aberrations can be adjusted or eliminated if the patient was bothered by optical side-effects caused by the primary lens system. Because the possible multiple images or astigmatism distortion suffered by the patient as a result of wound healing and the like cannot always be predicted preoperatively, as well as long-term medical or retinal changes be predicted, the ability to easily remove unwanted visual aberrations or inappropriate optical devices is critical to any versatile long-term refractive procedure.

Figure 1:
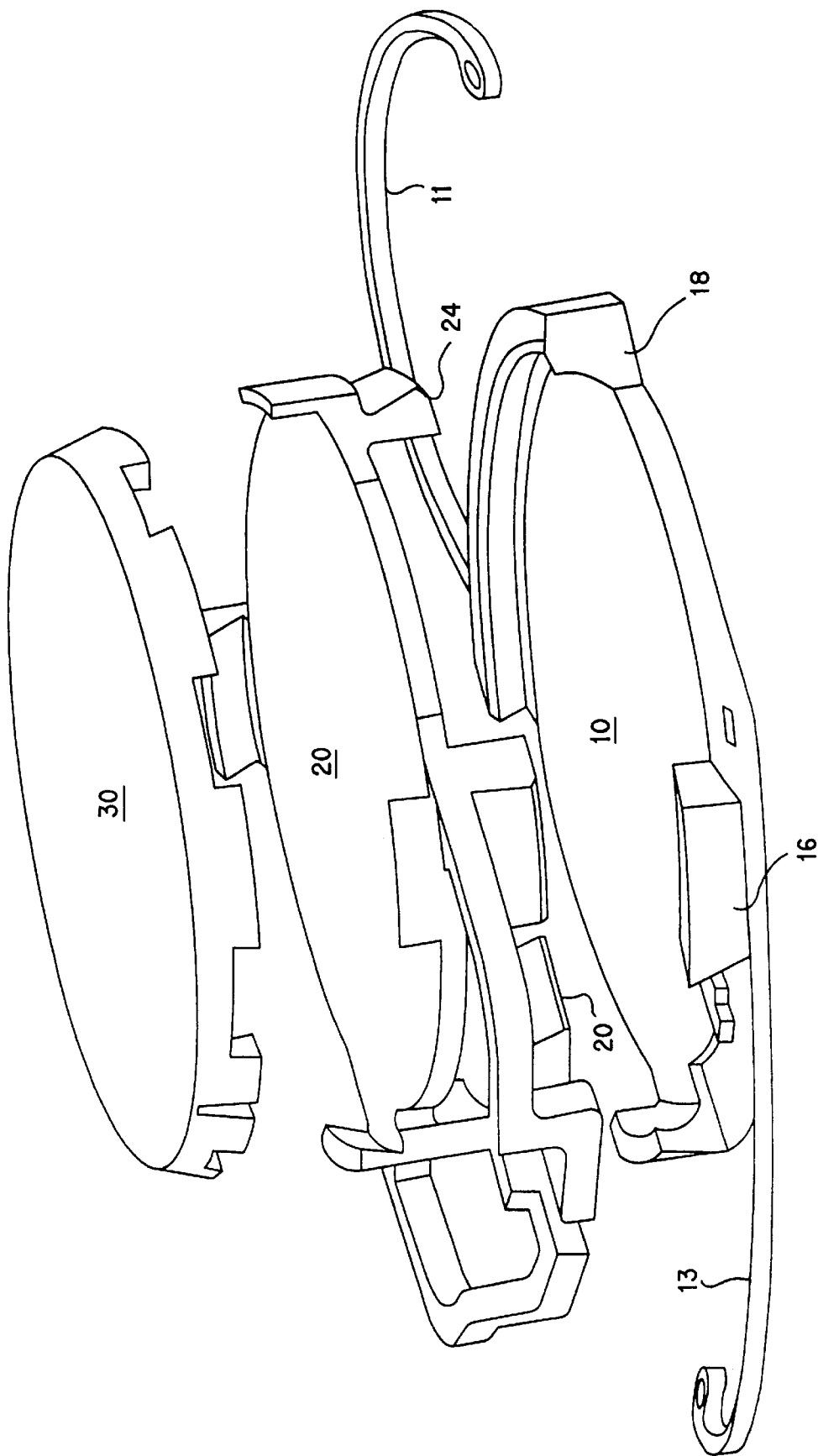
FIG. 1 is a plan view of the base, cap, and sandwich components of the multi-component intraocular lens.
Figure 2:
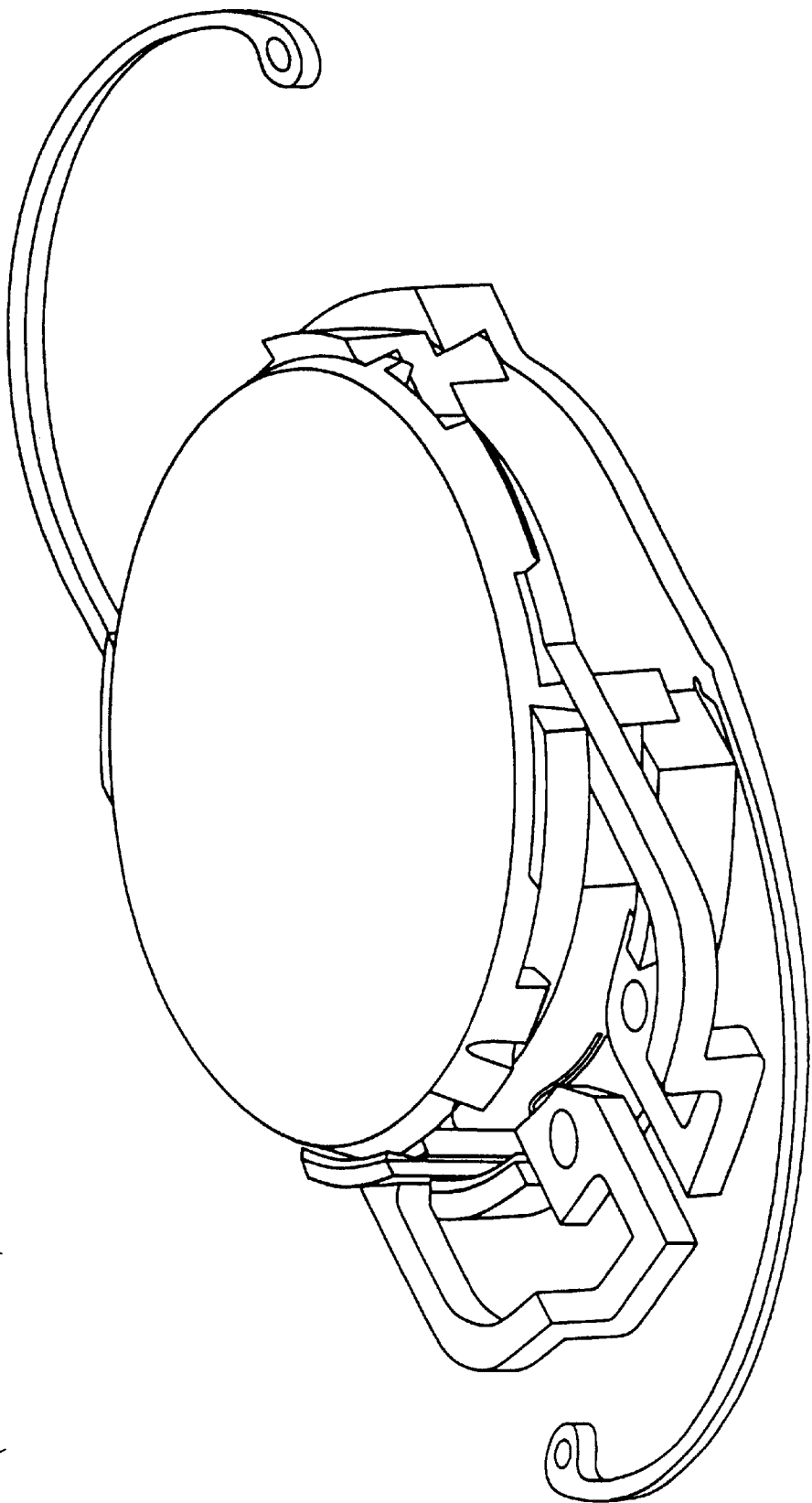
FIG. 2 is an exploded side view of the assembled base, sandwich and cap lenses of the multi-component intraocular lens.
Figure 3A:
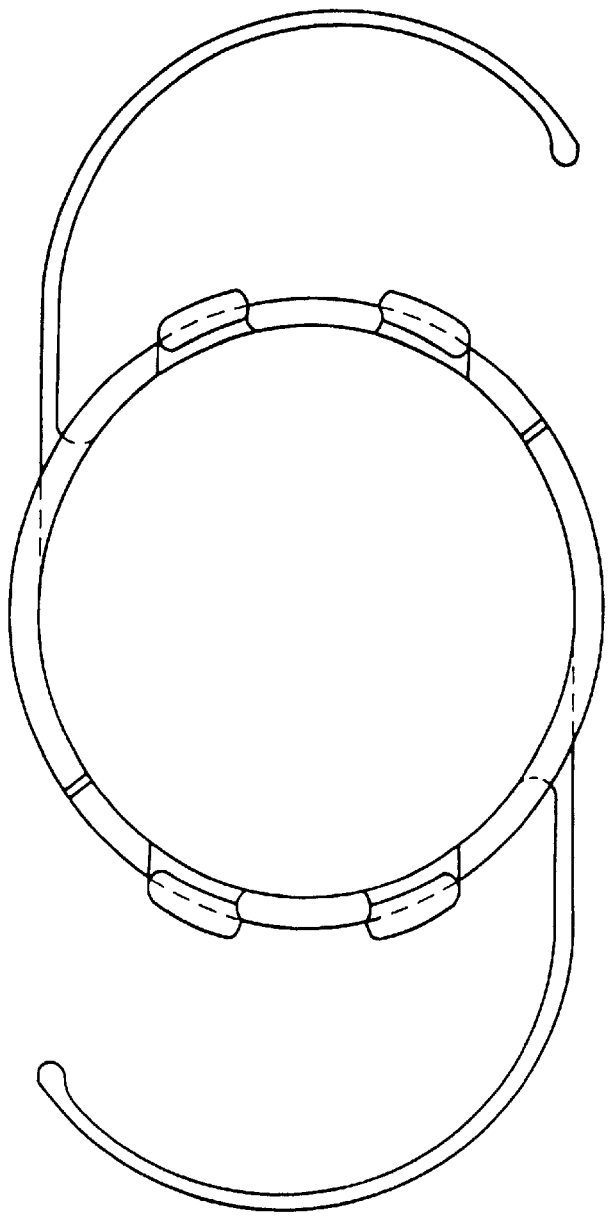
FIGS. 3A–3B are exploded views of a two component compound intraocular lens.
Figure 3B:
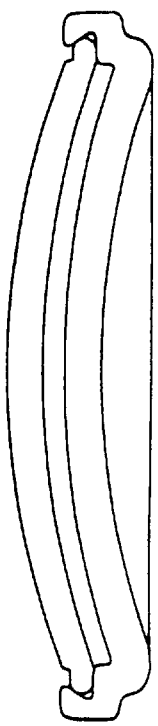
Figure 6:
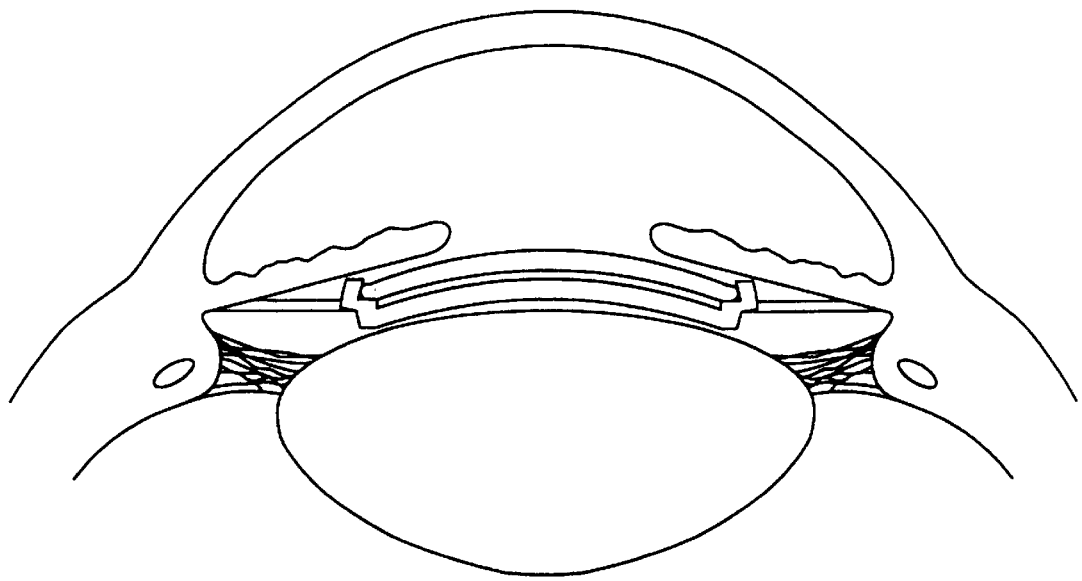
FIG. 6 is a side view of a compound intraocular lens implanted within a human eye ciliary sulcus.
Figure 7:
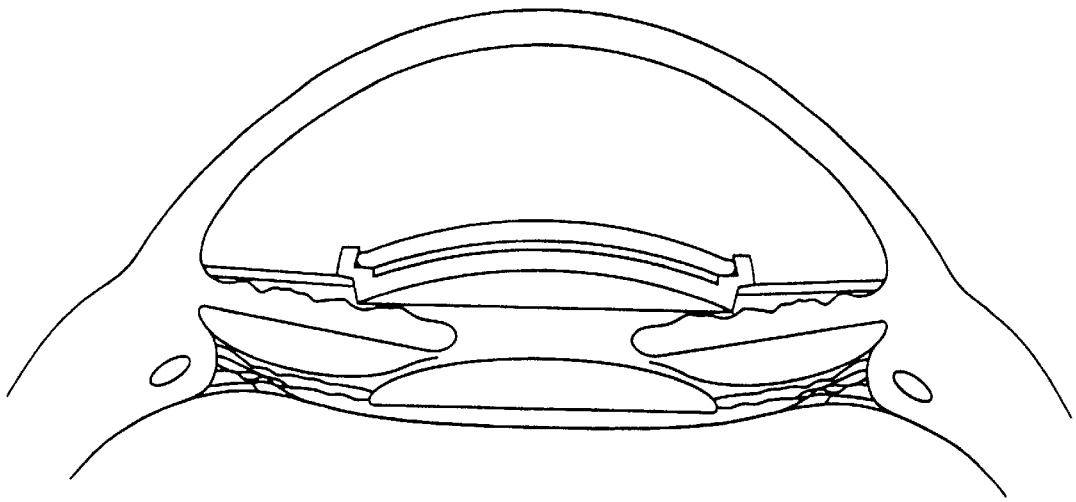
FIG. 7 is a side view of another compound intraocular lens implanted within a human eye using the anterior chamber angle as support.
Figure 8:
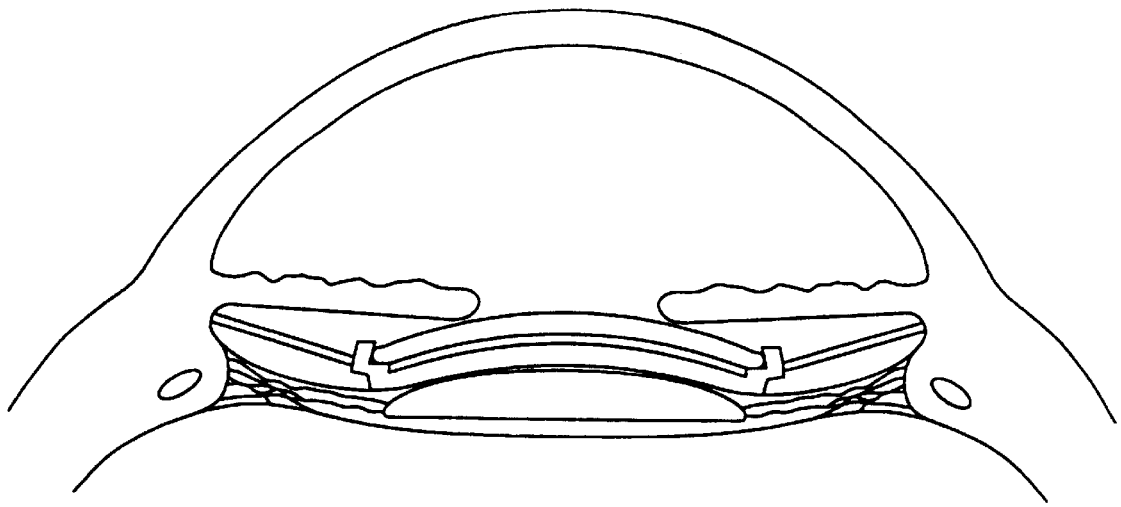
FIG. 8 is a side view of a sulcus mounted compound intraocular lens implanted within a human eye with a previously implanted single component conventional intraocular lens mounted in the capsular bag.
Figure 9:
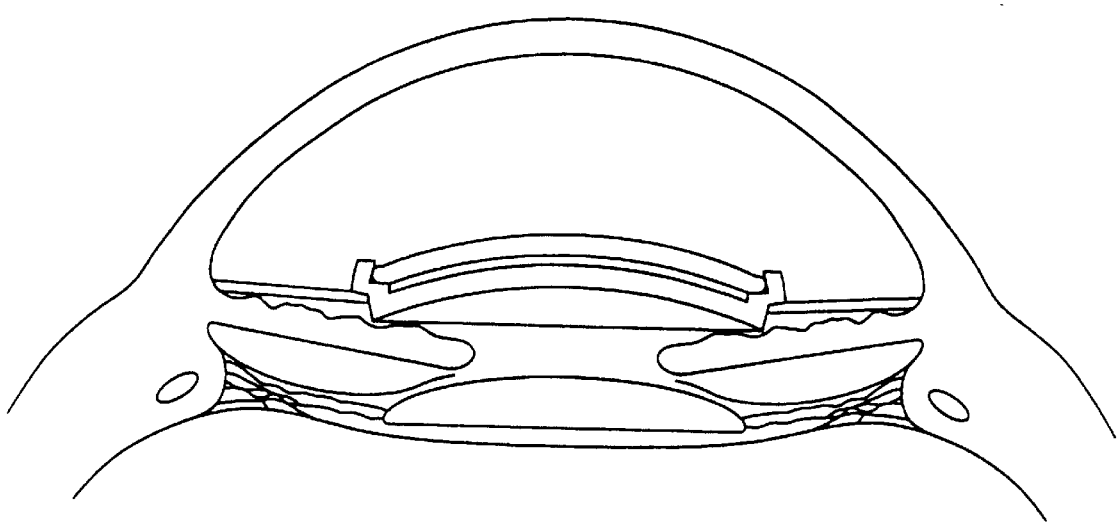
FIG. 9 is a side view of an anterior chamber mounted compound intraocular lens implanted within a human eye with a previously implanted single component conventional intraocular lens mounted in the capsular bag.
Figure 10:
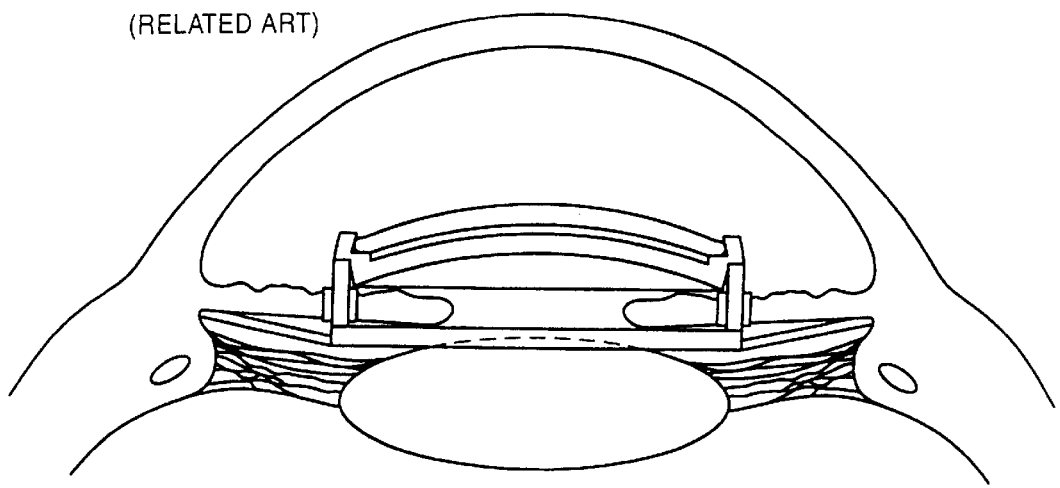
FIG. 10 is a side view of an anterior chamber mounted compound intraocular lens on a support secured in the posterior chamber and is implanted within a human eye with a previously implanted single component conventional intraocular lens mounted in the capsular bag.
Figure 11:
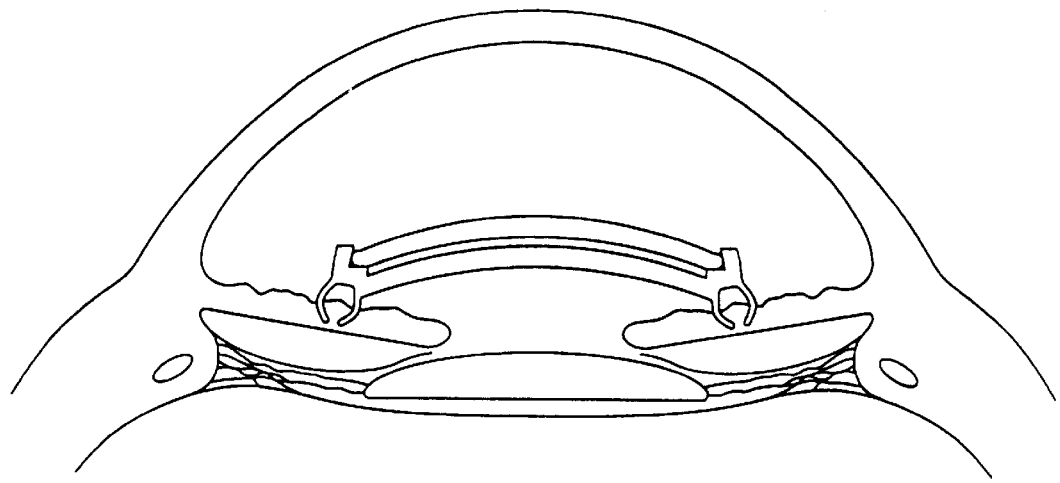
FIG. 11 is a side view of an iris fixated compound intraocular lens in the anterior chamber that is implanted within a human eye with a previously implanted single component conventional intraocular lens mounted in the capsular bag.
Figure 12:
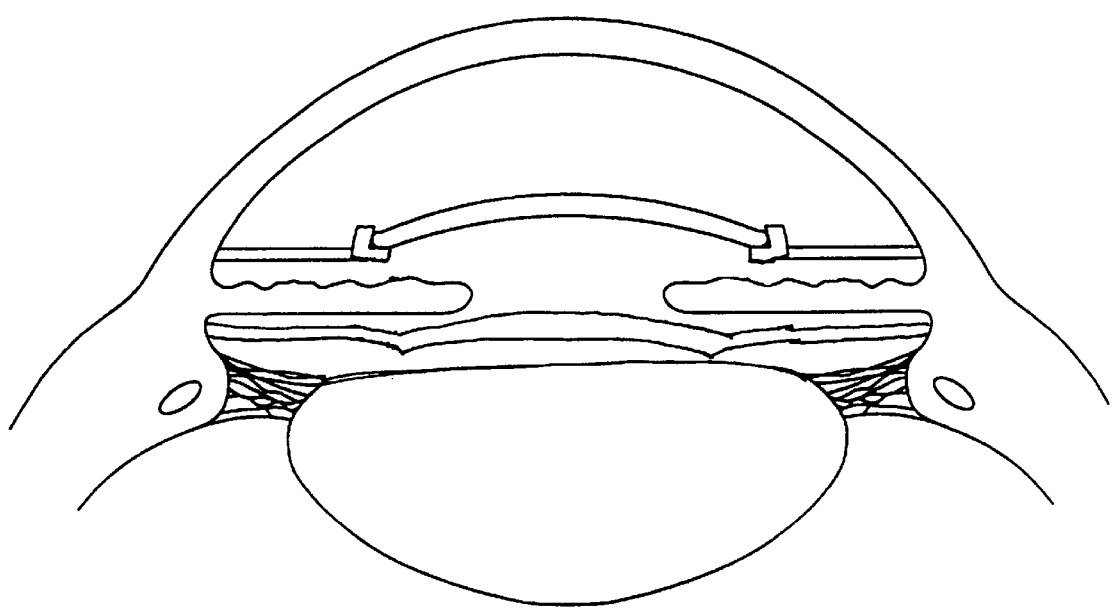
FIG. 12 is a side view of a single component exchangeable anterior chamber lens used in combination with a previously implanted single component conventional posterior chamber lens.

Referring to FIG. 12, the steps for carrying out the inventive concept of this application according to a preferred method are illustrated. In step 100, the method is started. Then, in step 110, the optical aberrations and optical abnormalities are identified within the optical system with, for example, wave front technology. It should be noted that the optical system is considered to comprise the eye of a mammal, such as, for example, a human, with or without the crystalline lens therein, and an intraocular lens implanted therein. The intraocular lens can be a single or permanent lens as well as a multi-component or compound lens, each or which has at least one removable component having at least one modifiable surface.

Figure 13:
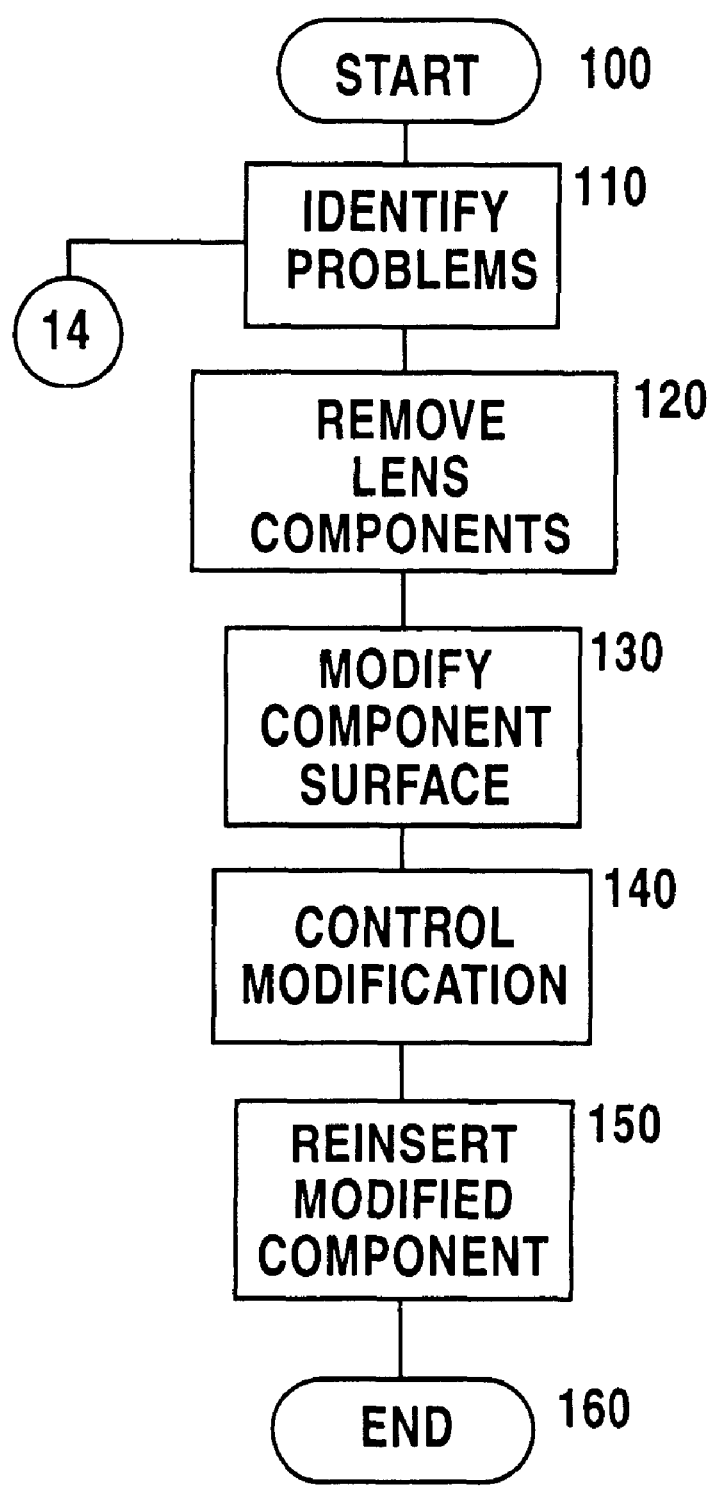
FIG. 13 is a flow chart illustrating the steps for carrying out the inventive concept of this application according to a preferred embodiment.

The optical aberrations and optical abnormalities are identified by measuring the optical system using wave front technology. Although it is within the scope of this invention to use other known or later developed measuring technologies, wave front analysis technology is discussed herein for the remainder of this application merely to simplify the explanation. FIG. 13 illustrates the basic steps for analyzing the properties of optical systems using wave front analysis.

In step 211, a light beam is focused on the fovea. Then, in step 212, a wave front sensor measures the wave aberrations and/or abnormalities of the human eye. Next, in step 213, the aberrations and/or abnormalities are determined by sensing the wave front emerging from the eye produced by the retinal reflection of the focused light beam on the fovea while discounting or eliminating the unwanted light reflected from other surfaces, such as the lenses and cornea of the eye.

This is accomplished because it is desirable to accurately measure, to a higher order, the aberrations of the eye and use the data thus measured to compensate for those aberrations by using a surface modifier to modify a surface of the intraocular lens to correct the aberrations. It should be noted that the aberrations and/or abnormalities that are to be corrected can be present on the eye or a customized optical element, such as, for example, an implanted intraocular lens provided within the eye. Preferably, a wave front sensor is used to measure the wave front in the plane of the pupil.

Then, because the sensor is typically connected to a digital CCD camera, in step 214, the CCD camera captures the image of the wave aberration and/or abnormalities of the eye. Next, in step 215, the output from the digital CCD is sent to a computer which accurately calculates the wave aberration and/or abnormalities. Then, in step 216, the analysis of the optical properties is completed and the method continues to step 120 of FIG. 12.

Next, in step 120, at least one of the removable components of the lens implanted in the eye is removed. Then, in step 130, the surface of at least one of the removable components is modified using a surface modifier.

A surface modifier is used to modify either a surface of the eye itself or a component, removable or fixed, of the intraocular lens. Preferably, the surface modifier will be a laser, such as, for example, an excimer laser. Furthermore, although a laser is discussed herein as the surface modifier, it should be noted that it is within the scope of this application to use any other known or subsequently developed surface modifiers. For example, an ultrasonic wave emitter can be used to emit ultrasonic waves to impinge upon any aberrations or abnormalities on the surface of the eye or component of the intraocular lens to eliminate such an aberration or abnormality.

Thus, a permanent intraocular lens can be modified once the optical aberration of the eye has been measured prior to any surgical event. However, it should be noted that this would not be as effective because the surgery itself induces additional optical aberrations. But, if there is a significant amount of pre-existing optical aberrations, then one can eliminate at least a large part of these aberrations by approximating what the final optical properties may be with an initial rather than a two-step operative procedure.

Also, it should be noted that it is within the scope of this application that any intraocular lens material, such as polymethylmethacrylate or PMMA, that is compatible with the surface modifier can be used. In other words, the material from which the intraocular lens is comprised of should be compatible with lasers, such as the excimer, as well as an ultrasonic wave emitter, in addition to any future developed surface modifiers and/or laser technology.

In step 140, a controller is used to control the duration and intensity of the modification performed by the surface modifier. The extent of the duration and intensity of the modification is a product of the actual wave front data resulting from the images transferred to the computer by the digital CCD camera. In other words, for example, the excimer laser will emit a laser beam that contacts a selected portion of the lens or eye corresponding to the results of the wave front analysis. The intensity of the laser beam and duration of contact are selected to provide conditions that are sufficient to alter the lens or eye, thereby altering or correcting the corrective power of the eye or lens.

Then, in step 150, the surface modified removable components of the lens is reinserted with the MC-IOL or C-IOL, ideally through the very wound which was used to implant the lens. Preferably, all of the optical aberrations and optical abnormalities are eliminated as a result of the above-described methods. Next, in step 160, the method is completed. Thus, the characteristics of the optical systems within the patient's eyes are improved in a safe and efficient manner.

Next, in step 160, the method is completed. In other words, with the lens in the eye, the total optical aberration of the eye can be measured. Then, the appropriate surface of the intraocular lens can be treated appropriately, and modifications performed on the surface such that the aberrations are corrected.

Figure 14:
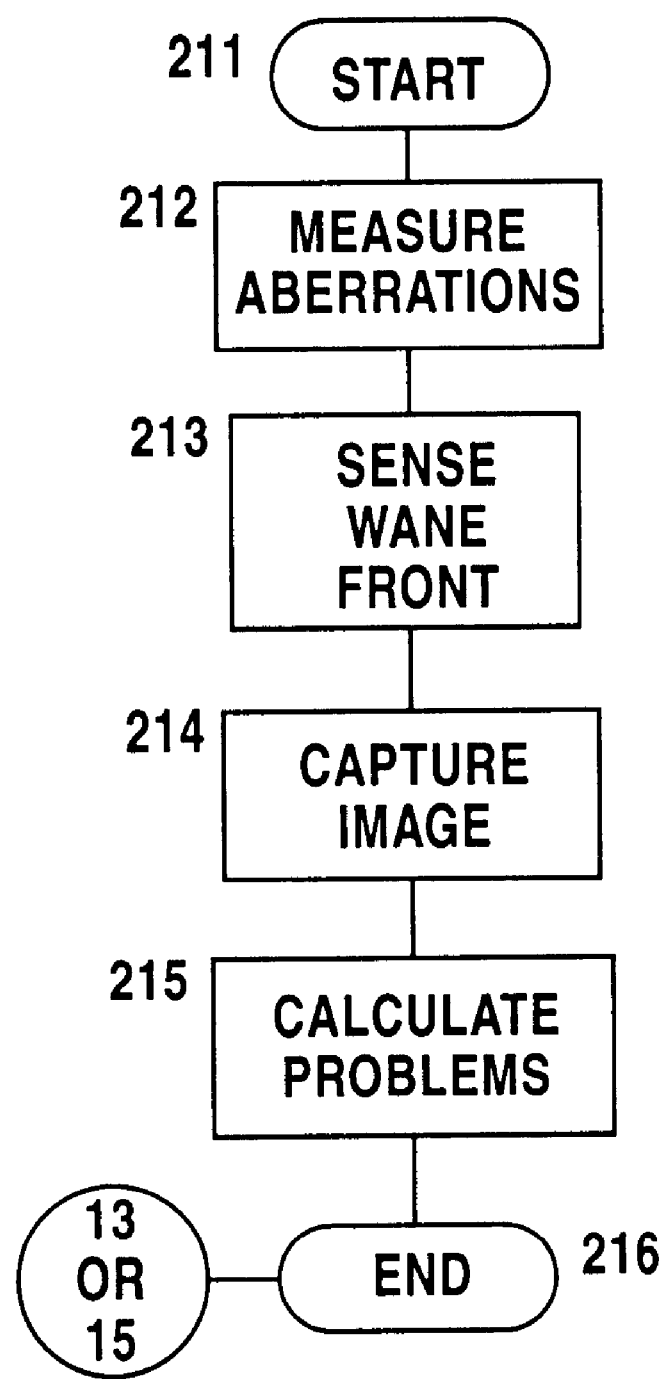
FIG. 14 is a flow chart illustrating the steps for carrying out wave front analysis.

Referring to FIG. 14, the steps for carrying out the inventive concept of this application according to another embodiment are illustrated. In step 300, the method is started. Then, in step 310, the optical aberrations and optical abnormalities are identified within the optical system, with, for example, wavefront technology. Again, as discussed above, the optical system is considered to comprise the eye of a mammal or human, with or without the crystalline lens therein, and an intraocular lens implanted therein. The intraocular lens can be a single or permanent lens as well as a multi-component or compound lens.

FIG. 13 illustrates the basic steps for analyzing the properties of optical systems using wave front analysis. As discussed above, it is within the scope of this invention to use other known or later developed measuring technologies, but wave front technology is discussed herein merely to simplify the explanation. Furthermore, as the steps illustrated in FIG. 13 have been discussed above, discussion of such is omitted to avoid redundancy with the exception of once the analysis of the optical system is complete, the method continues to step 320 of FIG. 14 wherein the optical aberrations and/or abnormalities of the optical system are modified.

The surface modifier is used to modify either a surface of the eye itself or a component, removable or fixed, of the intraocular lens while still in the optical system of the eye. In other words, components of the intraocular lens are not removed from the eye but rather are maintained therein. Preferably, the surface modifier will be a laser, but unlike the method of FIG. 12, an excimer laser is inapplicable with this method. The excimer laser is ineffective with intraocular lens components that are not removed from the eye simply because the excimer laser is absorbed by the cornea of the eye.

Accordingly, the inventor recognized that a YAG ™ laser, which is commonly used to remove the posterior capsule during cataract surgery, could be used as the surface modifier to modify the shape of the intraocular lens component(s) while still in the eye. Furthermore, when the intraocular lens is made of an unpolymerized PMMA or similar plastic material, an extended energy source could be used as the surface modifier to regionally polymerize the plastic lens in the eye to modify the shape of the lens component(s). Then, in step 330, a controller is used to control the duration and intensity of the modification performed by the surface modifier. As discussed above, the intensity and duration of contact of the surface modifier are selected to provide conditions sufficient to alter the lens or the eye, thereby altering or correcting the corrective power of the eye or lens. Next, in step 340, the method is completed.

While the invention has been described in conjunction with specific embodiments therefor, it is evident that various changes and modifications may be made, and the equivalents substituted for elements thereof without departing from the true scope of the invention. In addition, many modifications may be made to adapt a particular situation or material to the teachings of the invention without departing from the scope thereof. Therefore, it is intended that this invention not be limited to the particular embodiment disclosed herein, but will include all embodiments within the spirit and scope of the disclosure.

What is claimed is:

1. A method of correcting at least one of optical aberrations and optical abnormalities within an optical system of an eye having either one of a multi-component intraocular lens, a compound intraocular lens and a pair of single component intraocular lenses previously implanted therein for visual rehabilitation, the multi-component intraocular lens and compound intraocular lens each having at least one removable component, the method comprising the steps of:
    measuring and defining the optical aberrations and optical abnormalities within the optical system;
    removing the at least one removable component of either one of the multi-component intraocular lens and the compound intraocular lens after measuring and defining the optical aberrations and optical abnormalities;
    modifying the at least one surface using a surface modifier to eliminate the optical aberrations and optical abnormalities after removing the at least one removable component of either one of the multi-component intraocular lens and the compound intraocular lens; and
    reinserting the modified one of the multi-component intraocular lens and compound intraocular lens into the optical system of the eye.

2. The method according to claim 1, wherein the measuring and defining are performed using wave front analysis.

3. The method according to claim 2, wherein the modifying of the at least one surface is performed using a light emitting source.

4. The method according to claim 1, wherein the multi-component intraocular lens and compound intraocular lens each comprise a material modifiable by the surface modifier.

5. The method according to claim 4, wherein the material of each of the multi-component intraocular lens and the compound intraocular lens comprises polymethylmethacrylate.

6. The method according to claim 1, wherein the surface modifier comprises a light emitting source.

7. The method according to claim 6, wherein the light emitting source comprises a laser.

8. The method according to claim 7, wherein the laser comprises an excimer laser.

9. The method according to claim 1, wherein the surface modifier comprises and ultrasonic wave emitter.

10. The method according to claim 1, further comprising the step of controlling the duration and intensity of the surface modifier modifying the at least one surface of the intraocular lens.

11. The method according to claim 1, wherein a controller is used to perform the controlling step.

12. The method according to claim 11, wherein the controller comprises a computer.

13. The method according to claim 1, wherein the multi-component intraocular lens comprises a base lens having at least one projection to hold the multi-component lens in the eye to form a platform, a cap lens that attaches to a top of the base lens, and a sandwich lens held in position by the base lens.

14. The method according to claim 13, wherein the multi-component intraocular lens replaces a crystalline lens of the eye.

15. The method according to claim 13, wherein the at least one removable component comprises at least one of the cap lens and the sandwich lens.

16. The method according to claim 1, wherein the compound intraocular lens is usable with a preexisting lens within the eye and comprises a cap lens and a sandwich lens.

17. The method according to claim 16, wherein the preexisting lens is a crystalline lens of the eye.

18. The method according to claim 17, wherein the compound intraocular lens is positioned in one of either a sulcus of the eye or an anterior chamber angle of the eye.

19. The method according to claim 16, wherein the preexisting lens is an intraocular lens.

20. The method according to claim 19, wherein the compound intraocular lens is mounted in one of either a sulcus of the eye, anterior chamber angle of the eye, an anterior chamber with posterior chamber fixation, and anterior chamber with iris fixation.

21. The method according to claim 1, wherein either one of the multi-component intraocular lens and the compound intraocular lens are structured either as a monofocal and multi-focal optical system.

22. The method according to claim 1, wherein either one of the multi-component intraocular lens and the compound intraocular lens comprise chemically treated materials.

23. The method according to claim 22, wherein the chemically treated materials comprise either one of ultraviolet light-absorbing and tinted materials.

24. The method according to claim 1, wherein the pair of single component intraocular lenses comprise an adjustable anterior chamber lens and an adjustable posterior chamber lens.

25. The method according to claim 24, wherein the pair of single component intraocular lenses provide a refractive capability.

26. The method according to claim 25, wherein the refractive capability comprises telescopic vision.

27. A modified multi-component intraocular lens implanted in the optical system of a human eye having at least one removable component which has been removed from the lens, modified in accordance with a prior measurement of one of optical aberrations and optical abnormalities within the optical system, and reinserted into the lens following such modification.

28. A modified compound intraocular lens implanted in the optical system of a human eye including at least one removable component which has been removed from the lens, modified in accordance with a prior measurement of one of optical aberrations and optical abnormalities within the optical system, and reinserted into the lens following such modification.

29. The modified multi-component intraocular lens according to claim 27, wherein the prior measurement is preformed using wave front analysis.

30. The modified multi-component intraocular lens according to claim 27, wherein the at least one removable component of the multi-component intraocular lens removed from the lens comprises a material modifiable by a surface modifier.

31. The modified multi-component intraocular lens according to claim 30, wherein the material modifiable by the surface modifier comprises polymethylmethacrylate.

32. The modified multi-component intraocular lens according to claim 27, wherein at least one surface of the at least one removable component of the multi-component intraocular lens removed from the lens is modified using a light emitting source.

33. The modified multi-component intraocular lens according to claim 32, wherein the light emitting source comprises a laser.

34. The modified multi-component intraocular lens according to claim 33, wherein the laser comprises an excimer laser.

35. The modified multi-component intraocular lens according to claim 30, wherein the surface modifier comprises one of a light emitting source and an ultrasonic wave emitter.

36. The modified multi-component intraocular lens according to claim 30, wherein a controller controls a duration and intensity of the surface modifier modifying the modifiable material of the at least one removable component of the multi-component intraocular lens removed from the lens.

37. The modified multi-component intraocular lens according to claim 36, wherein the controller comprises a computer.

38. The modified multi-component intraocular lens according to claim 27, comprising a base lens having at least one projection to hold the multi-component lens in the eye to form a platform, a cap lens that attaches to a top of the base lens, and a sandwich lens held in position by the base lens.

39. The modified multi-component intraocular lens according to claim 38, wherein the at least one removable component comprises at least one of the cap lens and the sandwich lens.

40. The modified multi-component intraocular lens according to claim 27, wherein the lens is structured either as a monofocal and multi-focal optical system.

41. The modified multi-component intraocular lens according to claim 27, wherein the lens comprises chemically treated materials.

42. The modified multi-component intraocular lens according to claim 27, wherein the chemically treated materials comprise either one of ultraviolet light-absorbing and tinted materials.

43. The modified multi-component intraocular lens according to claim 27, wherein the lens replaces a crystalline lens of the eye.

44. The modified compound intraocular lens according to claim 28, wherein the prior measurement is preformed using wave front analysis.

45. The modified compound intraocular lens according to claim 28, wherein the at least one removable component of the compound intraocular lens removed from the lens comprises a material modifiable by a surface modifier.

46. The modified compound intraocular lens according to claim 45, wherein the material modifiable by a surface modifier comprises polymethylmethacrylate.

47. The modified compound intraocular lens according to claim 28, wherein at least one surface of the at least one removable component of the compound intraocular lens removed from the lens is modified using a light emitting source.

48. The modified compound intraocular lens according to claim 47, wherein the light emitting source comprises a laser.

49. The modified compound intraocular lens according to claim 48, wherein the laser comprises an excimer laser.

50. The modified compound intraocular lens according to claim 45, wherein the surface modifier comprises one of a light emitting source and an ultrasonic wave emitter.

51. The modified compound intraocular lens according to claim 45, wherein a controller controls a duration and intensity of the surface modifier modifying the modifiable material of the at least one removable component of the compound intraocular lens removed from the lens.

52. The modified compound intraocular lens according to claim 51, wherein the controller comprises a computer.

53. The modified compound intraocular lens according to claim 28 is usable with a preexisting lens within the eye and comprises a cap lens and a sandwich lens.

54. The modified compound intraocular lens according to claim 53, wherein the preexisting lens is either one of a crystalline lens of the eye and an intraocular lens.

55. The modified compound intraocular lens according to claim 28, wherein the lens is mounted in one of either a sulcus of the eye, an anterior chamber angle of the eye, an anterior chamber with posterior chamber fixation, and anterior chamber with iris fixation.

56. The modified compound intraocular lens according to claim 28, wherein the lens comprises chemically treated materials.

57. The modified compound intraocular lens according to claim 28, wherein the chemically treated materials comprise either one of ultraviolet light-absorbing and tinted materials.

58. The modified compound intraocular lens according to claim 28, wherein the lens is structured as a monofocal and multi-focal optical system.

* * * * *